United States Patent [19]
Mukai et al.

[11] Patent Number: 5,302,630
[45] Date of Patent: Apr. 12, 1994

[54] DENTAL ADHESIVE COMPOSITION

[75] Inventors: Nobuhiro Mukai; Takayuki Makino, both of Otake, Japan

[73] Assignee: Mitsubishi Rayon Co., Ltd., Tokyo, Japan

[21] Appl. No.: 545,653

[22] Filed: Jun. 29, 1990

[30] Foreign Application Priority Data

Aug. 14, 1989 [JP] Japan .................................. 1-207879

[51] Int. Cl.$^5$ ...................... C08F 230/08; C08F 4/40; A61K 6/083
[52] U.S. Cl. .................... 523/118; 523/116; 524/533; 525/264; 526/279
[58] Field of Search ............... 526/279, 328; 523/118, 523/116; 524/533; 525/264

[56] References Cited

U.S. PATENT DOCUMENTS

| | | | |
|---|---|---|---|
| 4,323,348 | 4/1982 | Schmitz-Josten et al. | 523/116 |
| 4,407,984 | 10/1983 | Ratcliffe et al. | 523/116 |
| 4,478,990 | 10/1984 | Kohno et al. | 526/279 |
| 4,650,845 | 3/1987 | Hegel | 526/301 |
| 4,713,403 | 12/1987 | Yoshida et al. | 523/116 |
| 4,725,631 | 2/1988 | Bastioli et al | 523/116 |
| 4,843,136 | 6/1989 | Reiness et al. | 526/279 |

FOREIGN PATENT DOCUMENTS

| | | |
|---|---|---|
| 0287516 | 10/1988 | European Pat. Off. |
| 0301516 | 2/1989 | European Pat. Off. |
| 0347711 | 12/1989 | European Pat. Off. |
| 1-193310 | 8/1989 | Japan .................................. 526/279 |

*Primary Examiner*—Paul R. Michl
*Assistant Examiner*—Andrew E. C. Merriam
*Attorney, Agent, or Firm*—Oblon, Spivak, McClelland, Maier & Neustadt

[57] ABSTRACT

A dental adhesive composition comprising, as the main components, (a) a polymer powder obtained by radical copolymerization of at least one (meth)acrylate unsaturated monomer containing no carboxyl or anhydride group in its molecule, with a silane compound having a polymerizable unsaturated group, (b) at least one radical polymerizable unsaturated monomer, and (c) a radical polymerization initiator.

7 Claims, No Drawings

DENTAL ADHESIVE COMPOSITION

The present invention relates to a dental adhesive composition having excellent adhesiveness, which is useful for bonding restorative materials (such as metals, organic polymeric materials and ceramic materials) to living tooth tissues.

Heretofore, as an adhesive for bonding restorative materials (particularly metallic materials) to living tissues, an adhesive has been- proposed which is of such a type that a powder and a liquid will be mixed for use at the time of practical use. Namely, a powder component composed of an inorganic powder or a polymer powder, and a liquid component obtained by incorporating a phosphate compound, a trimellitate or a silane compound as the adhesive component to a mixture of radical polymerizable unsaturated monomers, are mixed, polymerized and cured at room temperature by a radical polymerization initiator.

In most cases, such an adhesive is required to be polymerized and cured within a temperature range around normal temperature (room temperature) in a short period of time (usually in about 3 to 6 minutes) to provide a desired function, from the viewpoint of its practical application. A composition containing a phosphate compound is usually regarded as being excellent in the adhesive properties. However, when it is practically used, it can not necessarily be said to be excellent in the adhesive properties, since it is poor in the redox polymerizability (e.g. in a combination of a peroxide and an aromatic amine) at a room temperature. Further, in a case of a composition containing a (meth)acrylate monomer having a carboxyl or anhydride group, the initial adhesive strength is good, but it absorbs water and thus is very poor in the water resistance, since it contains the hydrophilic acidic functional group. On the other hand, a composition comprising a silane compound as the adhesive component and a radical polymerizable unsaturated monomer simply mixed thereto, is also very poor in the water resistance, and it is incapable of providing strong adhesion to tooth tissues over a long period of time under such an wet and temperature-changeable environment like in the mouth, although its initial adhesiveness may be adequate.

Under these circumstances, the present inventors have conducted extensive studies and, as a result, have found that the above mentioned problems of the conventional techniques can all be solved by preliminarily radical-copolymerizing a (meth)acrylate unsaturated monomer containing no carboxyl or anhydride group in its molecule and a silane compound having a polymerizable unsaturated group, so that a silane compound bonded by a covalent bond will be present in the polymer. The present invention has been accomplished on the basis of this discovery.

It is an object of the present invention to provide a novel dental adhesive having remarkably improved the water resistance which used to be a problem in bonding restorative materials, particularly metallic materials, to living tooth tissues, and yet having practically adequate adhesive strength.

The present invention provides a dental adhesive composition comprising, as the main components, (a) a polymer powder obtained by radical copolymerization of at least one (meth)acrylate unsaturated monomer containing no carboxyl or anhydride group in its molecule, with a silane compound having a polymerizable unsaturated group, (b) at least one radical polymerizable unsaturated monomer, and (c) a radical polymerization initiator.

Now, the present invention will be described in detail with reference to the preferred embodiments.

The (meth)acrylate unsaturated monomer containing no carboxyl or anhydride group in its molecule, which constitutes component (a) of the present invention, may be mono-functional or polyfunctional. Specific examples of the mono-functional (meth)acrylate unsaturated monomer containing no carboxyl or anhydride group in its molecule, include methyl (meth)acrylate, ethyl (meth)acrylate, benzyl (meth)acrylate, and glycidyl (meth)acrylate. Among them, methyl methacrylate or benzyl methacrylate is preferably employed.

Specific examples of the bifunctional (meth)acrylate monomer containing no carboxyl or anhydride group in its molecule, include ethylene glycol dimethacrylate, diethylene glycol dimethacrylate, triethylene glycol dimethacrylate, 1,6-hexanediol dimethacrylate, neopentyl glycol dimethacrylate, 2,2-bis[4-(3-methacryloyloxy-2hydroxypropoxy)phenyl]propane, 2,2-bis[4-(methacryloyloxy diethoxy)phenyl]propane, and 2,2-bis[4-(methacryloyloxypolyethoxy)phenyl]propane. Among them, ethylene glycol dimethacrylate, triethylene glycol dimethacrylate, or 2,2-bis[4-(3-methacryloyloxy-2-hydroxypropoxy)phenyl]propane is preferably employed.

Specific examples of the tri- or higher functional (meth)acrylate monomer containing no carboxyl or anhydride group in its molecule, include trimethylolpropane tri(meth)acrylate, tetramethylolmethane tri(meth)acrylate, and tetramethylolmethane tetra(meth)acrylate.

Further, an isocyanuric acid skeletal hexa-functional urethane (meth)acrylate of the formula (1):

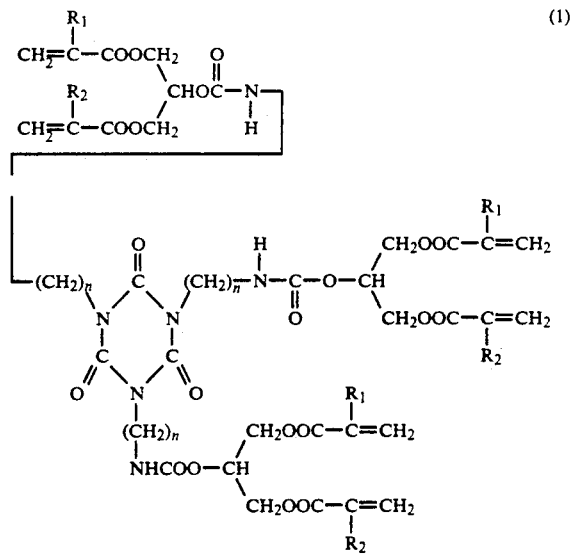

(wherein n is an integer of from 1 to 10, and each of $R_1$ and $R_2$ is a hydrogen atom or a methyl group), may also be used. As its specific examples, a hexa-functional urethane acrylate of the formula (1) wherein n=6, $R_1$ is a hydrogen atom, and $R_2$ is a methyl group (hereinafter referred to simply as U-6HA), and a hexa-functional urethane methacrylate of the formula (1) wherein n=6, and each of $R_1$ and $R_2$ is a methyl group, may preferably be employed.

Likewise, a tetra-functional urethane (meth)acrylate of the formula (2):

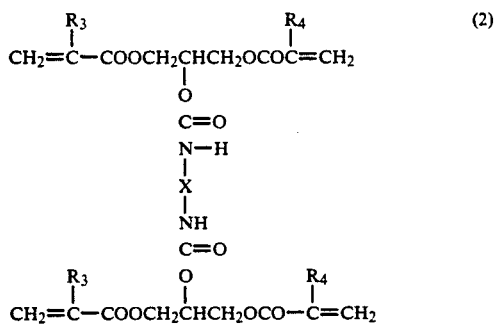

(wherein each of $R_3$ and $R_4$ independently represents a hydrogen atom or a methyl group, and X is a

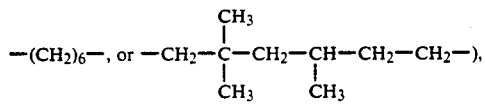

may also be used. As its specific examples, a tetrafunctional urethane (meth)acrylate of the formula (2) wherein $R_3$ is a hydrogen atom, $R_4$ is a methyl group, and X is $-(CH_2)_6-$ (hereinafter referred to simply as U-4HA) and a tetrafunctional urethane methacrylate of the formula (2) wherein each of $R_3$ and $R_4$ is a methyl group, and X is $-(CH_2)_6-$, may preferably be employed.

The silane compound having a polymerizable unsaturated group constituting component (a) of the present invention, is preferably the one copolymerizable with a radical polymerizable unsaturated monomer i.e. the one having a polymerizable unsaturated group in it molecule, among commonly employed silane coupling agents. Specific examples thereof include vinyl triethoxysilane, vinyl tris($\beta$-methoxy-ethoxy)silane, $\gamma$-methacryloyloxypropyltrimethoxysilane, and vinylsilyltriisocyanate. Among them, $\gamma$- (methacryloyloxypropyltrimethoxysilane, vinyl triethoxysilane, or vinylsilyltriisocyanate is preferably employed.

With respect to the blend ratio of the (meth)acrylate monomer containing no carboxyl or anhydride group in its molecule and the silane compound having a polymerizable unsaturated group for the preparation of the polymer powder, it is common to employ the silane compound having a polymerizable unsaturated group in an amount within a range of from 1 to 50% by weight relative to said monomer. If the silane compound having a polymerizable unsaturated group is used in an amount exceeding this range, the structural strength of the adhesive layer after curing, will be lost, and the water resistance will be lost, although the adhesive properties may be maintained.

As the radical polymerization initiator, dicumyl peroxide, benzoyl peroxide, azobisisobutyronitrile or the like, may be used in an amount of from about 0.01 to 5% by weight, based on the total amount of the mixture comprising the above monomer and the silane having a polymerizable unsaturated group.

Said polymer powder can be produced by a usual radical polymerization method using the above components as the main constituting elements. As its specific method, a mixture comprising such components is polymerized under atmospheric pressure by a method such as bulk polymerization, suspension polymerization, solution polymerization or emulsion polymerization. In some cases, the product may be mechanically pulverized to obtain a desired polymer powder.

The dental adhesive composition of the present invention is used in such a form that the obtained polymer powder and the radical polymerizable unsaturated monomer constituting component (b) of the present invention are mixed. However, when a clinical operation is intended, it is preferred that the powder and the liquid can easily be mixed and can readily be made into a paste. In such a case, the shape of the polymer powder may be spherical or non-specific. However, the average particle size is preferably within a range of from 0.01 to 200 $\mu$m. Even if the polymer powder does not have a crosslinked structure, its degree of polymerization may be within a wide range, but preferably is within a range of from 10 to 1,000.

The radical polymerizable unsaturated monomer as component (b) of the present invention, may be monofunctional or polyfunctional. However, such a monomer preferably has a (meth)acryloyloxy group in its structure.

Among such monomers, specific examples of the monofunctional unsaturated monomer include methyl (meth)acrylate, ethyl (meth)acrylate, propyl (meth)acrylate, butyl (meth)acrylate, pentyl (meth)acrylate, hexyl (meth)acrylate, 2-hydroxyethyl (meth)acrylate, glycidyl methacrylate, benzyl methacrylate, and methacryloyloxyethyl phosphate. Among them, methyl acrylate, methyl methacrylate, benzyl methacrylate, 2-hydroxyethyl methacrylate, or metharyloyloxyethyl phosphate, can preferably be employed.

As an example of the bifunctional unsaturated monomer, a polyethylene glycol di(meth)acrylate of the following formula (3):

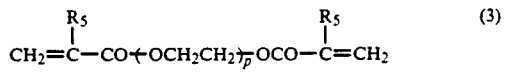

(wherein $R_5$ is a hydrogen atom or a methyl group, and p is an integer of from 1 to 20), may be employed. Specific examples thereof include ethylene glycol di(meth)acrylate, diethylene glycol di(meth)acrylate, triethylene glycol di(meth)acrylate, tetraethylene glycol di(meth)acrylate, pentaethylene glycol di(meth)acrylate, hexaethylene glycol di(meth)acrylate, heptaethylene glycol di(meth)acrylate, octaethylene glycol di(meth)acrylate, nonaethylene glycol di(meth)acrylate, decaethylene glycol di(meth)acrylate, a polyethylene glycol di(meth)acrylate with a number of ethylene glycol unit (p) being 14, a polyethylene glycol di(meth)acrylate with p being 17, and a polyethylene glycol di(meth)acrylate with p being 19. Among them, ethylene glycol di(meth)acrylate, triethylene glycol di(meth)acrylate, nonaethylene glycol di(meth)acrylate, or a polyethylene glycol (meth)diacrylate with p being 14, is preferably employed.

Further, 1,6-hexanediol di(meth)acrylate, neopentyl glycol (meth)acrylate, trimethylolpropane tri(meth)acrylate, and dimethacryloyloxyethylphosphate, may also be employed. Among them, trimethylol propane triacrylate, 1,6-hexanediol di(meth)acrylate, or dimethacryloyloxyethylphosphate, is preferably employed.

Further, bisphenol A type (meth)acrylates of the following formula (4):

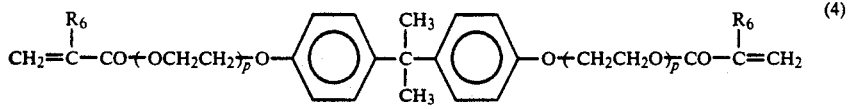

(wherein $R_6$ is a hydrogen atom or a methyl group, and p is an integer of from 1 to 20), and of the following formula (5):

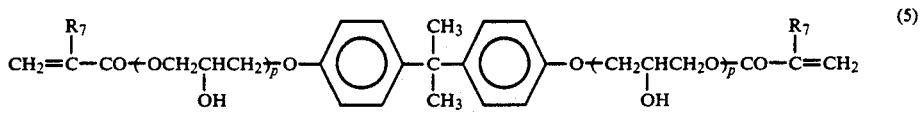

(wherein each $R_7$ independently represents a hydrogen atom or a methyl group, and p is an integer of from 1 to 20), may also be employed. Specific examples thereof include 2,2-bis(4-methacryloyloxypolyethoxyphenyl)-propane and 2,2-bis[4-(3-methacryloyloxy-2-hydroxypropoxy)phenyl]propane. Also, 2,2-bis[3-(meth)acryloyloxy-2-hydroxypropoxy]ethane, and 1,4-bis[3-(meth)acryloyloxy-2-hydroxypropoxy]butane may be employed.

Further, a tetra-functional urethane (meth)acrylate of the formula (2):

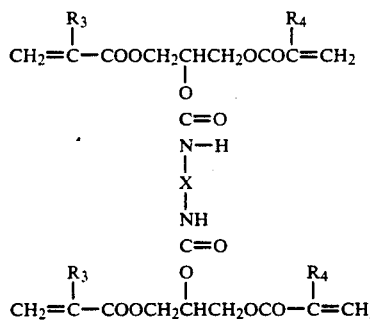

(wherein $R_3$, $R_4$ and X are as defined above), may also be employed. Specific examples thereof include a tetravalent urethane (meth)acrylate of the formula (2) wherein $R_3$ is a hydrogen atom, $R_4$ is a methyl group, and X is —$(CH_2)_6$— (hereinafter referred to simply as U-4HA), and a tetra-functional methacrylate of the formula (2) wherein each of $R_3$ and $R_4$ is a methyl group, and X is —$(CH_2)_6$— (hereinafter referred to simply as U-4H).

As the polymerization initiator of component (c) of the present invention, a combination of an amine with a peroxide, a sulfinate with a peroxide, or an amine-sulfinate with a peroxide, is preferably used.

As the peroxide, conventional radical polymerization catalysts such as diacetyl peroxide, dilauroyl peroxide, distearyl peroxide, dibenzoyl peroxide, and di-p-chlorobenzoyl peroxide, may be used. Among them, dibenzoyl peroxide is particularly preferred, since it is excellent in room temperature polymerizability.

The amine may be a primary, secondary or tertiary amine. However, from the viewpoint of room temperature polymerizability, a tertiary amine is preferably used.

Specific examples of preferred aromatic amines include N,N-dimethylaniline, N,N-diethylaniline, N,N-di($\beta$-hydroxyethyl)aniline, N,N-dimethyl-p-toluidine, N,N-diethyl-p-toluidine, N,N'-di($\beta$-hydroxyethyl)-p-toluidine, N-methylaniline, N-methyl-p-toluidine, N,N-dimethylanisidine, N,N-diethylanisidine, and diphenylamine. Among them, N,N-dimethyl-p-toluidine, and N,N'-di($\beta$-hydroxyethyl)-p-toluidine are particularly preferred, since they are excellent in room temperature polymerizabilily.

As the sulfinate, sodium p-toluenesulfinate, sodium benzenesulfinate, potassium benzenesulfinate, calcium benzenesulfinate, barium benzenesulfinate, and ammonium benzenesulfinate, may be used. Among them, sodium p-toluenesulfinate is particularly preferred, since it is excellent in room temperature polymerizability.

Such a redox polymerization initiator is preferably added so that the peroxide will be within a range of from 0.01 to 10% by weight, more preferably within a range of from 0.05 to 5% by weight, relative to the total radical polymerizable unsaturated monomers, and the aromatic amine or sulfinate will be within a range of from 0.01 to 10% by weight, more preferably within a range of from 0.05 to 5% by weight.

The dental adhesive composition of the present invention comprises the above three components as the main components. If necessary, however, inorganic filler (such as silica powder, quartz powder or various glass powders), a coloring agent, a polymerization inhibitor (such as hydroquinone), an antioxidant, an ultraviolet absorber, a pigment, a dyestuff, etc. may be incorporated.

The dental adhesive composition of the present invention is conveniently stored in such a state that the above three components are not mixed until its practical use. However, it is also acceptable that the aromatic amine and the sulfinate are incorporated to the polymer compound of component (a), while the peroxide is incorporated to the radical polymerizable unsaturated monomer, and they are stored separately and will be mixed at the time of the practical use.

The dental adhesive composition of the present invention can be applied to various restorative materials, and it is capable of providing excellent adhesive properties when applied to e.g. amalgam, alumina, gold, or an alloy material commonly employed as a prosthetic material in this field, and a thermosetting material such as a composite resin (a composite material having an inorganic filler incorporated to a polyfunctional monomer), or a resin for crowns, as well as to a thermoplastic resin such as polymethyl methacrylate, polysulfone, or polycarbonate, which is used as a resin for denture, or to various cement materials.

tions and the average particle sizes are shown in Table 1.

TABLE 1

| Identification of the polymer powder | Polymerization initiator | (Meth)acrylate unsaturated monomer containing no acidic group in its molecule | Vinyl silane compound | Average particle size (μm) |
| --- | --- | --- | --- | --- |
| Preparation Example-2 (F-2) | AIBN | Benzyl methacrylate (25 g) | *1)γ-methacryloyloxypropyl-trimethoxysilane (5 g) | 0.5 |
| Preparation Example-3 (F-3) | AIBN | 1G (25 g) | *1)γ-methacryloyloxypropyl-trimethoxysilane (5 g) | 0.9 |
| Preparation Example-4 (F-4) | AIBN | 3G (25 g) | *1)γ-methacryloyloxypropyl-trimethoxysilane (5 g) | 13 |
| Preparation Example-5 (F-5) | AIBN | MMA (15 g), 3G (10 g) | *1)γ-methacryloyloxypropyl-trimethoxysilane (5 g) | 20 |
| Preparation Example-6 (F-6) | AIBN | Bis-GMA (10 g), 3G (15 g) | *1)γ-methacryloyloxypropyl-trimethoxysilane (5 g) | 65 |
| Preparation Example-7 (F-7) | AIBN | U-4HA (10 g), 1G (15 g) | *1)γ-methacryloyloxypropyl-trimethoxysilane (5 g) | 52 |
| Preparation Example-8 (F-8) | AIBN | U-4HA (10 g), MMA (15 g) | *1)γ-methacryloyloxypropyl-trimethoxysilane (5 g) | 38 |
| Preparation Example-9 (F-9) | AIBN | TMM (10 g), 3G (15 g) | *1)γ-methacryloyloxypropyl-trimethoxysilane (5 g) | 80 |
| Preparation Example-10 (F-10) | AIBN | 3G (25 g) | *2)vinyltriethoxysilane (5 g) | 7 |
| Preparation Example-11 (F-11) | AIBN | Bis-GMA (10 g), 3G (15 g) | *2)vinyltriethoxysilane (5 g) | 60 |
| Preparation Example-12 (F-12) | AIBN | U-4HA (10 g), MMA (15 g) | *2)vinyltriethoxysilane (5 g) | 41 |
| Preparation Example-13 (F-13) | AIBN | 3G (15 g) | *3)vinylsilyltriisocyanate (5 g) | 25 |
| Preparation Example-14 (F-14) | AIBN | Bis-GMA (10 g), 3G (15 g) | *3)vinylsilyltriisocyanate (5 g) | 57 |

*1)$CH_2 = CCH_3COO(CH_2)_3Si(OCH_3)$
*2)$CH_2 = CHSi(OC_2H_5)_3$
*3)$CH_2 = CHSi(NCO)_3$

With the dental adhesive composition of the present invention, high adhesive bond strength which can not be attained by the conventional techniques for bonding restorative materials to living tooth tissues, can be obtained, and it is excellent also in the water resistance over a long period of time.

Now, the present invention will be described in further detail with reference to Examples. However, it should be understood that the present invention is by no means restricted by such specific Examples.

PREPARATION EXAMPLE 1

Into a 500 ml glass separable flask, 300 g of toluene and 1.0 g of azobisisobutyronitrile (hereinafter referred to simply as AIBN) were charged. Then, 25 g of methyl methacrylate (hereinafter referred to simply as MMA) and 5 g of γ-methacryloyloxypropyltrimethoxysilane were charged, and the mixture was thoroughly stirred. Then, copolymerization was conducted by continuing the stirring at 70° C. for 5 hours. After completion of the polymerization, the product was put into a large amount of methanol, and unreacted substances were removed. Further, drying under reduced pressure was conducted for two hours. Then, the product was pulverized in a ball mill to obtain a polymer powder. From the electron microscopic observation, the shape of the particles was found to be non-specific, and the average particle size was found to be 30 μm. (This polymer powder will be referred to hereinafter as F-1.)

PREPARATION EXAMPLES 2 TO 14

Preparation of polymer powders was conducted in the same manner as in Preparation Example 1 except that the types of the (meth)acrylate unsaturated monomer containing no carboxyl or anhydride group in its molecule and the silane compound having a polymerizable unsaturated group were changed. The compositions

COMPARATIVE PREPARATION EXAMPLES 1 TO 3

Preparation of polymer powders was conducted in the same manner as in Preparation Example 1 except that a radical polymerizable unsaturated monomer containing a carboxyl group in its molecule was used, and a silane compound having a polymerizable unsaturated group was not used. The compositions are shown in Table 2. Identifications:

| 1G: | ethylene glycol dimethacrylate |
| --- | --- |
| 3G: | triethylene glycol dimethacrylate |
| TMM: | trimethylolpropane trimethacrylate |
| Bis-GMA: | 2,2-bis[4-(3-methacryloyloxy-2-hydroxypropoxy)phenyl]propane |

TABLE 2

| Identification of the polymer powder | Polymerization initiator | Radical polymerizable unsaturated monomer containing acid group in its molecule | Vinyl silane compound |
| --- | --- | --- | --- |
| Comparative Preparation Example-1 (H-1) | AIBN | methacryl acid (25 g) | — |
| Comparative Preparation Example-2 (H-2) | AIBN | 4-methacryloyloxyethyl-trimellitic acid anhydride (25 g) | — |
| Comparative Preparation Example-3 (H-3) | AIBN | 3G (15 g). methacryl acid (10 g) | — |

To 5 g of a polymer powder prepared in one of the preceding Preparation Examples, 0.05 g of N,N-diethanol-p-toluidine and 0.02 g of p-toluenesulfinic acid were mixed. On the other hand, as a liquid component, a mixture comprising a monomer as identified in Table 3 and BPO (dibenzoyl peroxide: 1.0% by weight relative to said monomer) was prepared.

TABLE 3

| Identification of liquid component | Monomer composition |
| --- | --- |
| L-1 | MMA (100 parts by weight) |
| L-2 | MMA (60 parts by weight), 3G (40 parts by weight) |
| L-3 | MMA (40 parts by weight), 3G (40 parts by weight), HEMA (20 parts by weight) |
| L-4 | MMA (30 parts by weight), Bis-GMA (70 parts by weight) |
| L-5 | U-4HA (40 parts by weight), 3G (50 parts by weight) |
| L-6 | MMA (90 parts by weight), γ-methacryloyloxypropyltrimethoxysilane (10 parts by weight) |

EXAMPLES 1 TO 22

A metal specimen of about 10 mm×10 mm having a flat surface was thoroughly polished with a water resistant polishing paper No. 1,000 under water flow to obtain a smooth surface. On this surface, the adhesive composition of the present invention (obtained by mixing the polymer powder and the liquid component in a weight ratio of 1:1) was coated, and then a rod of acrylic resin having a diameter of 4 mm was bonded thereto. One hour later, the metal specimen with the rod of acrylic resin bonded thereto, was immersed in water of 37° C. 24 hours later and 7 days later, the metal specimen was taken out from the water, and the tensile bond strength was measured by a tensile tester. The conditions for the measurement are shown below.

| Tensile tester: | Tensilone, manufactured by Toyo Boldwin Company. |
| --- | --- |
| Cross head speed (pulling speed): | 0.5 mm/min |
| Full scale: | 40 kg w |
| Metal used: | Gold-silver-plladium alloy (Castwell 12, trade name), manufactured by G-C Shika Kogyo K.K. |

The results of the tests are shown in Table 4.

TABLE 4

| | | Identification | Adhesive bond strength (kg/cm$^2$) | |
| --- | --- | --- | --- | --- |
| Example No. | Identification of the polymer powder | of the liquid component | Storage in water 1 day later | Storage in water 1 month later |
| Example 1 | Prep. Example 1 (F-1) | L-2 | 119 | 128 |
| Example 2 | Prep. Example 2 (F-2) | L-2 | 130 | 120 |
| Example 3 | Prep. Example 3 (F-3) | L-2 | 137 | 124 |
| Example 4 | Prep. Example 4 (F-4) | L-2 | 150 | 140 |
| Example 5 | Prep. Example 5 (F-5) | L-2 | 147 | 137 |
| Example 6 | Prep. Example 6 (F-6) | L-2 | 126 | 105 |
| Example 7 | Prep. Example 7 (F-7) | L-2 | 140 | 113 |
| Example 8 | Prep. Example 8 (F-8) | L-2 | 137 | 120 |
| Example 9 | Prep. Example 9 (F-9) | L-2 | 139 | 119 |
| Example 10 | Prep. Example 10 (F-10) | L-2 | 128 | 104 |
| Example 11 | Prep. Example 11 (F-11) | L-2 | 120 | 98 |
| Example 12 | Prep. Example 12 (F-12) | L-2 | 125 | 107 |
| Example 13 | Prep. Example 13 (F-13) | L-2 | 118 | 110 |
| Example 14 | Prep. Example 14 (F-14) | L-2 | 126 | 101 |
| Example 15 | Prep. Example 5 (F-5) | L-1 | 134 | 130 |
| Example 16 | Prep. Example 5 (F-5) | L-3 | 140 | 122 |
| Example 17 | Prep. Example 5 (F-5) | L-4 | 121 | 114 |
| Example 18 | Prep. Example 5 (F-5) | L-5 | 107 | 88 |
| Example 19 | Prep. Example 6 (F-6) | L-1 | 125 | 97 |
| Example 20 | Prep. Example 6 (F-6) | L-3 | 134 | 104 |
| Example 21 | Prep. Example 6 (F-6) | L-4 | 130 | 115 |
| Example 22 | Prep. Example 6 (F-6) | L-5 | 114 | 100 |

COMPARATIVE EXAMPLES 1 TO 9

The adhesive bond strength was evaluated in the same manner as in Example 1 except that the polymer powders prepared in the Comparative Preparation Examples were used. The results are shown in Table 5.

TABLE 5

| | | Identification | Adhesive bond strength (kg/cm$^2$) | |
| --- | --- | --- | --- | --- |
| Comparative Example No. | Identification of the polymer powder | of the liquid component | Storage in water 1 day later | Storage in water 1 month later |
| Comparative Example 1 | Comparative Prep. Example 1 (F-1) | L-2 | 78 | 43 |
| Comparative Example 2 | Comparative Prep. Example 2 (F-2) | L-2 | 80 | 24 |
| Comparative Example 3 | Comparative Prep. Example 3 (F-3) | L-2 | 54 | 15 |
| Comparative Example 4 | Comparative Prep. Example 2 (F-2) | L-1 | 50 | 12 |
| Comparative Example 5 | Comparative Prep. Example 2 (F-2) | L-3 | 61 | 34 |
| Comparative Example 6 | Comparative Prep. Example 2 (F-2) | L-4 | 54 | 27 |
| Comparative Example 7 | Comparative Prep. Example 2 (F-2) | L-5 | 76 | 19 |

TABLE 5-continued

| Comparative Example No. | Identification of the polymer powder | Identification of the liquid component | Adhesive bond strength (kg/cm$^2$) | |
|---|---|---|---|---|
| | | | Storage in water 1 day later | Storage in water 1 month later |
| Comparative Example 8 | Comparative Prep. Example 2 (F-2) | L-6 | 82 | 23 |
| Comparative Example 9 | Comparative Prep. Example 3 (F-3) | L-6 | 45 | 10 |

EXAMPLE 23

The adhesive bond strength was evaluated in the same manner as in Example 5 except that the metal species was changed to a nickel-chromium alloy (SB Bondlloy, trade name, manufactured by Sankin Kogyo K.K.), whereby the adhesive bond strength after one day was 142 kg/cm$^2$, and the adhesive bond strength after one month was 130 kg/cm$^2$.

With the dental adhesive composition of the present invention, a strong adhesive bond strength which can not be attained by the conventional techniques, is obtainable for the bonding restorative materials to living tooth tissues, and it is excellent also in the water resistance for a long period of time.

We claim:

1. A dental adhesive composition comprising, as the main components, (a) a polymer powder obtained by radical copolymerization of at least one (meth)acrylate unsaturated monomer containing no carboxyl or anhydride group in its molecule, with a silane compound having a polymerizable unsaturated group, (b) at least one radical polymerizable unsaturated monomer, and (c) a redox polymerization initiator consisting essentially of a combination of an organic peroxide and an aromatic amine and/or a sulfinate.

2. The dental adhesive composition according to claim 1, wherein said (meth)acrylate unsaturated monomer containing no carboxyl or anhydride group in its molecule, is at least one member selected from the group consisting of methyl (meth)acrylate, ethyl (meth)acrylate, benzyl (meth)acrylate, glycidyl (meth)acrylate, ethylene glycol dimethacrylate, diethylene glycol dimethacrylate, triethylene glycol dimethacrylate, 1,6-hexandiol dimethacrylate, neopentyl glycol dimethacrylate, 2,2-bis[4-(3-methacryloyloxy-2-hydroxypropoxy)phenyl]propane, 2,2-bis[4-(methacryloyloxydiethoxy)phenyl]propane, trimethylolpropane tri(meth)acrylate, tetramethylolmethane tri(meth)acrylate, tetramethylolmethane tetra(meth)acrylate, an isocyanuric acid skeletal hexa-functional urethane (meth)acrylate of the formula (1):

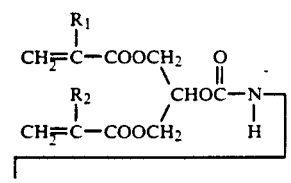

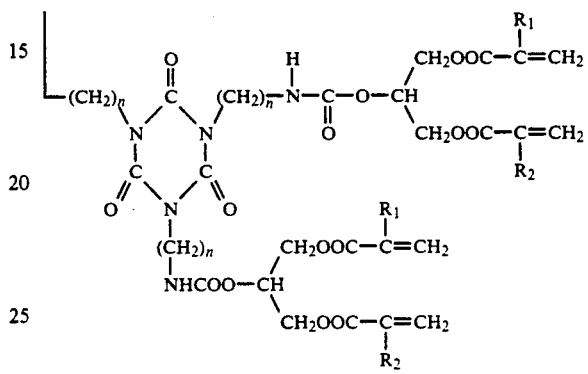

(wherein n is an integer of from 1 to 10, and each of R$_1$ and R$_2$ independently represents a hydrogen atom or a methyl group), and a tetra-functional urethane (meth)acrylate of the formula (2):

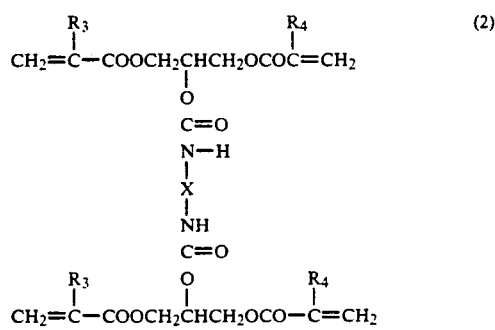

(wherein each of R$_3$ and R$_4$ independently represents a hydrogen atom or a methyl group, and X represents $-CH_2-$, $-CH_2CH_2-$, $-(CH_2)_3-$, $-(CH_2)_4-$, $-(CH_2)_5-$, $-(CH_2)_6-$, or $-CH_2-\underset{\underset{CH_3}{|}}{\overset{\overset{CH_3}{|}}{C}}-CH_2-CH-CH_2-CH_2-$).

3. The dental adhesive composition according to claim 1, wherein the silane compound having a polymerizable unsaturated group, is at least one member selected from the group consisting of γ-methacryloyloxypropyltrimethoxysilane, vinyl trichlorosilane, vinyl trimethoxysilane, vinylsilyl triisocyanate, 2-trimethoxysilyl-1,3-butadiene, and 3methacryloyloxypropylsilyl triisocyanate.

4. The dental adhesive composition according to claim 1, wherein the amount of the silane compound having a polymerizable unsaturated group is from 1 to 50% by weight relative to the (meth)acrylate unsaturated monomer containing no carboxyl or anhydride group in its molecule.

5. The dental adhesive composition according to claim 1, wherein the polymer powder has an average particle size of from 0.01 to 200 μm.

6. The dental adhesive composition according to claim 1, wherein the radical polymerizable unsaturated monomer is one having a (meth)acryloyloxy group.

7. The dental adhesive composition according to claim 6, wherein the radical polymerizable unsaturated monomer is at least one member selected from the group consisting of methyl (meth)acrylate, ethyl (meth)acrylate, propyl (meth)acrylate, butyl (meth)acrylate, pentyl (meth)acrylate, hexyl (meth)acrylate, 2-hydroxyethyl (meth)acrylate, glycidyl (meth)acrylate, benzyl (meth)acrylate, methacryloyloxyethyl phosphate, a polyethylene glycol di(meth)acrylate represented by the formula (3):

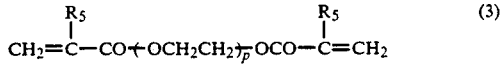

(wherein $R_5$ is a hydrogen atom or a methyl group, and p is an integer of from 1 to 20), 1,6-hexanediol di(meth)acrylate, neopentyl glycol di(meth)acrylate, trimethylolpropane tri(meth)acrylate, dimethacryloyloxyethyl phosphate, a bisphenol A di(meth)acrylate of the formula (4) or (5):

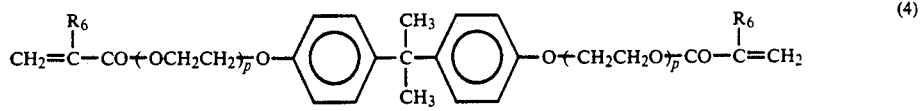

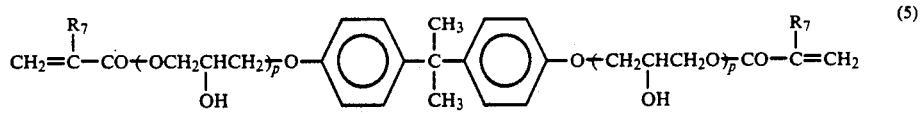

(wherein each of $R_6$ and $R_7$ independently represents a hydrogen atom or a methyl group, and p is an integer of from 1 to 20), 1,2-bis[3-(meth)acryloyloxy-2-hydroxypropoxy]ethane, 1,4-bis[3-(meth)acryloxyloxy-2-hydroxypropoxy]butane, a tetra-functional urethane (meth)acrylate of the formula (2):

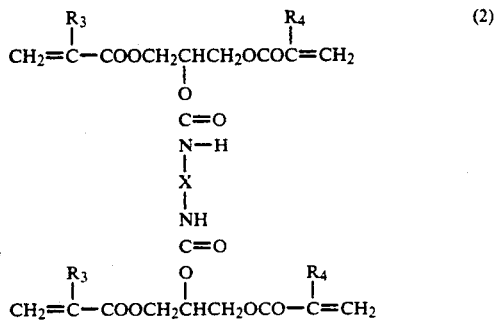

(wherein $R_3$, $R_4$ and $R_X$ are as defined above).

* * * * *